(12) United States Patent
Kim et al.

(10) Patent No.: US 6,426,995 B1
(45) Date of Patent: Jul. 30, 2002

(54) RADIATION INSPECTION SYSTEM AND METHOD USING THE SAME

(75) Inventors: Yong-won Kim, Suwon; Hyo-nam Joo; Hyeong-cheol Kim, both of Seongnam, all of (KR)

(73) Assignee: Samsung Electronics Co., Ltd., Suwon (KR)

( * ) Notice: Subject to any disclaimer, the term of this patent is extended or adjusted under 35 U.S.C. 154(b) by 30 days.

(21) Appl. No.: 09/688,807

(22) Filed: Oct. 17, 2000

(30) Foreign Application Priority Data

Feb. 16, 2000 (KR) .......................................... 2000-7377

(51) Int. Cl.7 ................................................ H05G 1/26
(52) U.S. Cl. ....................................... 378/98.3; 378/62
(58) Field of Search ............................... 378/124, 98.6, 378/58, 62, 138, 98.3, 86

(56) References Cited

U.S. PATENT DOCUMENTS

| | | | | |
|---|---|---|---|---|
| 4,516,252 A | * | 5/1985 | Linde et al. | 378/2 |
| 5,020,086 A | * | 5/1991 | Peugeot | 378/113 |
| 5,199,054 A | * | 3/1993 | Adams et al. | 378/21 |
| 5,259,012 A | * | 11/1993 | Baker et al. | 378/21 |
| 5,500,886 A | * | 3/1996 | Duff | 378/207 |
| 5,594,770 A | * | 1/1997 | Bowles et al. | 378/58 |
| 5,619,266 A | * | 4/1997 | Tomita et al. | 348/363 |
| 5,878,107 A | * | 3/1999 | Ishikawa et al. | 378/116 |
| 6,151,380 A | * | 11/2000 | Zweig et al. | 378/58 |
| 6,222,903 B1 | * | 4/2001 | Kim et al. | 378/22 |

* cited by examiner

*Primary Examiner*—Robert H. Kim
*Assistant Examiner*—Hoon K. Song
(74) *Attorney, Agent, or Firm*—Larson & Taylor PLC

(57) ABSTRACT

A radiation inspection system and a method using the same. The system includes a steering radiation electronic tube for generating radiation, and an image intensifier for converting a plurality of projection images formed by projecting the radiation from the steering radiation electronic tube onto an object to be inspected into visual images. The system also includes a visual image part on which the visual images are projected, an electronic shutter having a visual image transmission part for transmitting the visual images from the visual image part of the image intensifier in sequence, and a camera for photographing the visual images from the visual image transmission part of the electronic shutter in sequence. With this configuration, the electronic shutter transmits visual images sequentially.

12 Claims, 5 Drawing Sheets

RADIATION INSPECTION SYSTEM AND METHOD USING THE SAME

BACKGROUND OF THE INVENTION

1. Technical Field

The present invention relates in general to radiation inspection systems and methods using the same, and more particularly, to a radiation inspection system and a method using the same allowing visual images to be transmitted sequentially using an electronic shutter.

2. Description of the Related Art

Radiation includes α-rays, β-rays, σ-rays, X-rays, neutron-rays, etc. which cause electrolytic dissociation in reacting with materials. X-rays are electronic waves whose wavelengths are in the range of 10–0.001 nm, having such optical characteristics as reflection and diffraction, etc. The wavelengths can be exactly measured using a diffraction grating.

X-rays have a capability of transmitting or passing through an object. The rate of transmission varies depending upon materials, density and thickness of the object. An X-ray detection method uses this property of X-rays to detect thickness and position of a defective part in the object from the difference in photosensitive intensity of a film photographed by X-rays.

X-rays show the phenomenon of diffraction when transmitted into an object. An X-ray stress measuring method uses this property of X-rays to calculate stress by transmitting X-rays into the object and measuring from diffracted rays a dimensional variation in the distance between faces of a certain crystal lattice to which stress is applied.

A radiation inspection system is a typical non-destructive test (NDT) system which employs and systemizes the X-ray detection method and the X-ray stress measuring method. X-ray transmission characteristics vary depending upon materials, density and thickness of an object to be inspected, so that the X-rays are reflected into X-ray projecting images. The radiation inspection system converts the X-ray projecting images into visual images. The radiation inspection system performs a non-destructive test on a portion of the object which is invisible from the outside, based on the converted visual images.

FIG. 4 is a perspective view schematically showing a conventional radiation inspection system, and FIG. 5 is a perspective view partially showing some elements of the system of FIG. 4 from a different angle. As illustrated, the conventional radiation inspection system is comprised of an X-Y table 57 on which an object 53 to be inspected by NDT rests, an X-ray electronic tube 51 for generating X-rays and projecting the X-rays into the object 53, and an image intensifier 55 for forming visual images from the X-rays having passed through the object 53. The radiation inspection system is further comprised of an image selection unit 60 for selecting desired visual images among visual images formed by the image intensifier 55 and a charge coupled device (CCD) camera 65 for photographing the selected images and outputting them to an image sensor(not shown).

Between the X-ray electronic tube 51 and the image intensifier 55 is disposed the X-Y table 57 on which the object 53 rests and which is movable in X-Y directions. The image intensifier 55 is disposed on a transmission path of he X-rays generated by the X-ray electronic tube 51. On the lower face of the image intensifier 55 is provided a visual image part 56 on which the visual images formed through the image intensifier 55 are projected.

The image selection unit 60 is disposed along the transmission path of the X-rays under the visual image part 56, and comprises a primary galvanometer 61 and a secondary galvanometer 62. The primary galvanometer 61 has a rotary shaft parallel to the plane of the visual image part 56 and the secondary galvanometer 62 has a rotary shaft perpendicular to the plane of the visual image part 56. On the one end of the rotary shaft of the primary galvanometer 61 is mounted a primary reflector 63 for selectively reflecting the visual images from the visual image part 56. On the one end of the rotary shaft of the secondary galvanometer 61 is mounted a secondary reflector 64 for selectively reflecting the visual images reflected by the primary reflector 63, toward the CCD camera 65.

The image selection unit 60 further comprises a galvanometer controller 67 for controlling rotational angles of the primary galvanometer 61 and the secondary galvanometer 62 so as to selectively provide the CCD camera 65 with the visual images projected on the visual image part 56, through a reflection path optically formed by the primary reflector 63 and the secondary reflector 64.

The primary and secondary galvanometers 61 and 62 have very little moment of inertia, to thereby enable a precise servo control at high speed. Accordingly, the primary and secondary galvanometers 61 and 62 are capable of precisely rotating the primary and secondary reflectors 63 and 64 at high speed so as to reflect visual images on any part of the visual image part 56.

The conventional radiation inspection system operates n the following manner. The X-ray electronic tube 51 radiates X-rays toward the area to be inspected on the object 53 while being rotated along a circumferential direction at constant speed. Projected images formed by the X-rays having passed through the object 53 are circumferentially projected on the top face of the image intensifier 55. The projected images on the top face of the image intensifier 55 are converted into visual images through the inside of the image intensifier 55. The visual images are projected on the visual image part 56 positioned on the lower end of the image intensifier 55. The visual images projected on the visual image part 56 are selected by the image selection unit 60 and photographed by the CCD camera 65. The visual images photographed by the CCD camera 65 are synthesized and analyzed by a computer (not shown).

However, the conventional radiation inspection system results in high production cost because of the galvanometers 61 and 62 which are comparatively expensive as an image selection unit 60 for selecting visual images. Additionally, distortion of visual images may be caused by the primary and secondary reflectors 63 and 64 in the course of transferring the visual images to the CCD camera 65, thereby resulting in lowering a reliability of the inspection result.

To solve the above-described problems, a radiation inspection system has been proposed which provides a plurality of image intensifiers and a plurality of CCD cameras corresponding to the number of projected images formed by the X-rays, so that visual images formed through the image intensifier 55 can be directly transmitted into the respective CCD cameras. The radiation inspection system of this type is advantageous in photographing the visual images promptly and precisely, but it still requires a high cost of production.

SUMMARY OF THE INVENTION

Therefore, the present invention has been made in view of the above problems, and it is an object of the present invention to provide a radiation inspection system and a method for using the same allowing visual images to be photographed promptly and precisely, but with a lower cost of production.

In accordance with the present invention, the above and other objects can be achieved by the provision of a radiation inspection system comprising a steering radiation electronic tube for projecting radiation onto an object to be inspected, an image intensifier for converting a plurality of projection images formed by the radiation from the steering radiation electronic tube into visual images, the image intensifier having a visual image part on which the visual images are projected, an electronic shutter having a visual image transmission part for transmitting the visual images projected on the visual image part of the image intensifier in sequence, and a camera for photographing the visual images from the visual image transmission part of the electronic shutter in sequence.

Preferably, electric signals are applied synchronously with formation of the visual images to the visual image transmission part causing the sequential transmission of the visual images thereby.

Preferably, the visual image transmission part comprises a plurality of polarizing filters for transmitting or shielding the visual images according to the electric signals received thereby.

It is effective that the polarizing filters are formed of a liquid crystal display (LCD) or a plasma display panel (PDP).

Preferably, the visual images are formed sequentially along a circumferential direction of the visual image part, and the polarizing filters are disposed along a circumferential direction of the visual image transmission part so as to be correspondent with the visual images.

Preferably, the radiation includes X-rays.

According to another aspect of the present invention, the object can be achieved by a radiation inspection method using a radiation inspection system comprising the steps of: projecting radiation from a steering radiation electronic tube onto an object to be inspected, converting with an image intensifier a plurality of projection images formed by the radiation from the steering radiation electronic tube into visual images, the converting step including projecting the visual images onto a visual image part, providing an electronic shutter having a visual image transmission part corresponding to the visual images adjacent the visual image part, transmitting the visual images of the visual image part sequentially through the visual image transmission part, and photographing the visual images passing through the electronic shutter in sequence.

Preferably, the transmitting step includes applying electric signals synchronously with formation of the visual images to the visual image transmission part.

Preferably, the visual image transmission part comprises a plurality of polarizing filters for transmitting or shielding the visual images, and the transmitting step includes applying of the electric signals to the polarizing filters.

It is effective that the polarizing filters are formed of a liquid crystal display (LCD) or a plasma display panel (PDP).

Preferably, the converting step includes sequentially forming visual images along a circumferential direction of the visual image part, and the polarizing filters are disposed along a circumferential direction of the visual image transmission part so as to be correspondent with the visual images.

Preferably, the radiation projected from the steering radiation electronic tube includes X-rays.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION OF THE PREFERRED EMBODIMENTS

Hereinbelow, a radiation inspection system and method according to one embodiment of the present invention will be described in detail with reference to the accompanying drawings.

Figure 1:
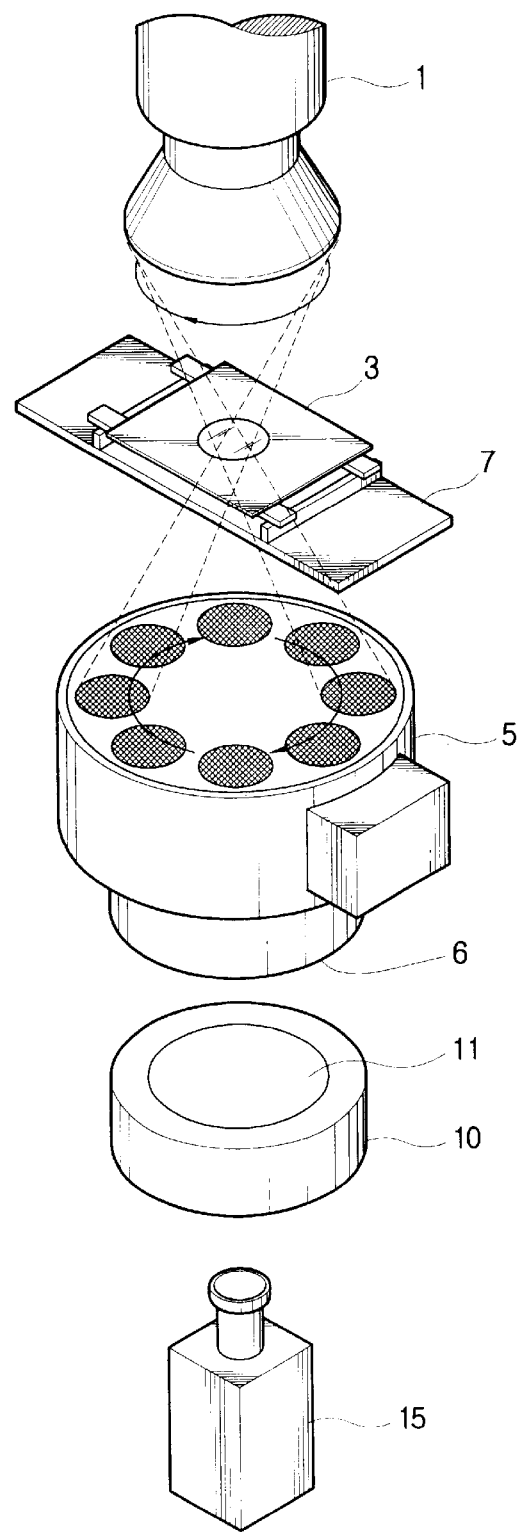
FIG. 1 schematically shows a perspective view of a radiation inspection system according to the present invention.
Figure 2:
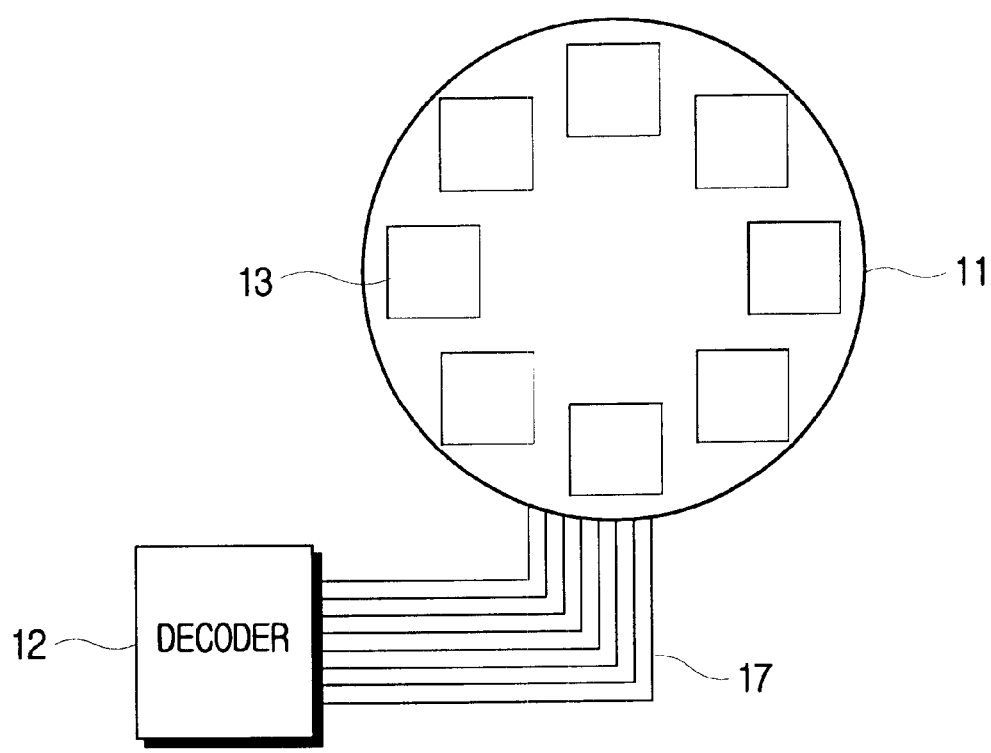
FIG. 2 shows a top plan view of a polarizing filter of an electronic shutter shown in FIG. 1.

FIG. 1 schematically shows a perspective view of a radiation inspection system according to one embodiment of the present invention, and FIG. 2 shows a top plan view of a polarizing filter of an electronic shutter shown in FIG. 1. As depicted therein, the radiation inspection system is comprised of an X-Y table 7 on which an object 3 to be inspected by an NDT rests, a steering X-ray electronic tube 1 for generating X-rays toward an inspection area on the object 3, an image intensifier 5 for forming visual images from the X-rays passing through the object 3 and having a visual image part 6 on which the visual images are projected, an electronic shutter 10 having a visual image transmission part 11 for transmitting the visual images from the image intensifier 5 in sequence, and a CCD camera for sequentially photographing the visual images from the electronic shutter 10 and outputting them to an image sensor (not shown).

Between the steering X-ray electronic tube 1 and the image intensifier 5 is disposed the X-Y table on which the object 3 rests and which is movable in X-Y directions.

The steering X-ray electronic tube 1 radiates the X-rays on the inspection area of the object 3 several times while being rotated at constant speed. Because the steering X-ray electronic tube 1 is rotated along the circumference of the image intensifier 5, a plurality of projection images formed by the X-rays passing through the object 3 are circumferentially disposed on the top face of the image intensifier 5. The projection images formed on the top face of the image intensifier 5 are invisible, and converted into visual images while passing through the inside of the image intensifier 5. The visual images are projected on the visual image part 5 along the circumferential direction thereof.

The electronic shutter 10 is, as illustrated in FIG. 2, comprised of the visual image transmission part 11 comprising a plurality of polarizing filters 13 for transmitting or shielding the visual images according to electric signals applied from a controller (not shown) for controlling the radiation inspection system synchronously with formation of the visual images, and a decoder 12 for allowing external electric power to be supplied to the respective polarizing filters 13 based on the electric signals from the controller for controlling the radiation inspection system. Each polarizing filter 13 is formed of an LCD or a PDP, is disposed along the circumference of the visual image transmission part 11 on the corresponding positions of the respective visual images projected on the visual image part 6. Polarizing filters 13 are respectively connected to corresponding cables 17. If electric power is supplied through each electric line 13 connected to each polarizing filter 13, light can be transmitted into each polarizing filter 13 and each visual image is projected toward the CCD camera 15 accordingly.

The radiation inspection system according to the present invention is operated in the following manner.

For NDT of the object 3 to be inspected, the steering X-ray electronic tube 1 generates X-rays during rotation and projects the X-rays to the inspection area of the object 3. The X-rays which pass through the object 3 are formed into visual images while passing through the image intensifier 5. The visual images are projected sequentially on the visual image part 6 provided on the lower face of the image intensifier 5. The controller applies the electric signals to the decoder 12 synchronously with formation of the visual images, to thereby supply electric power to each of the polarizing filters 13 corresponding to the visual images projected on the visual image part 6.

Figure 3:
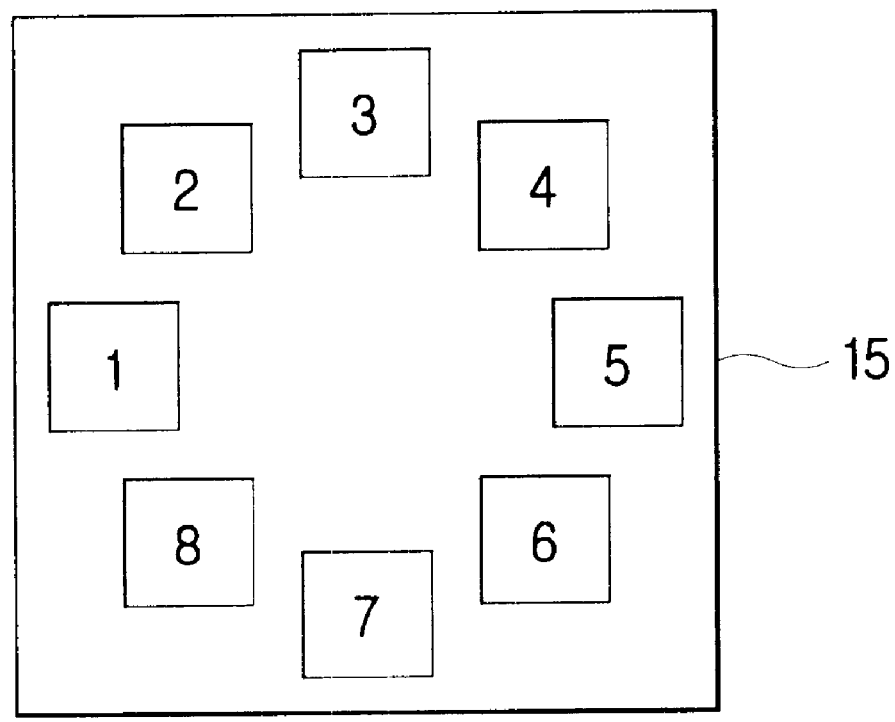
FIG. 3 shows a top plan view of images photographed by a camera shown in FIG. 1.
Figure 4:
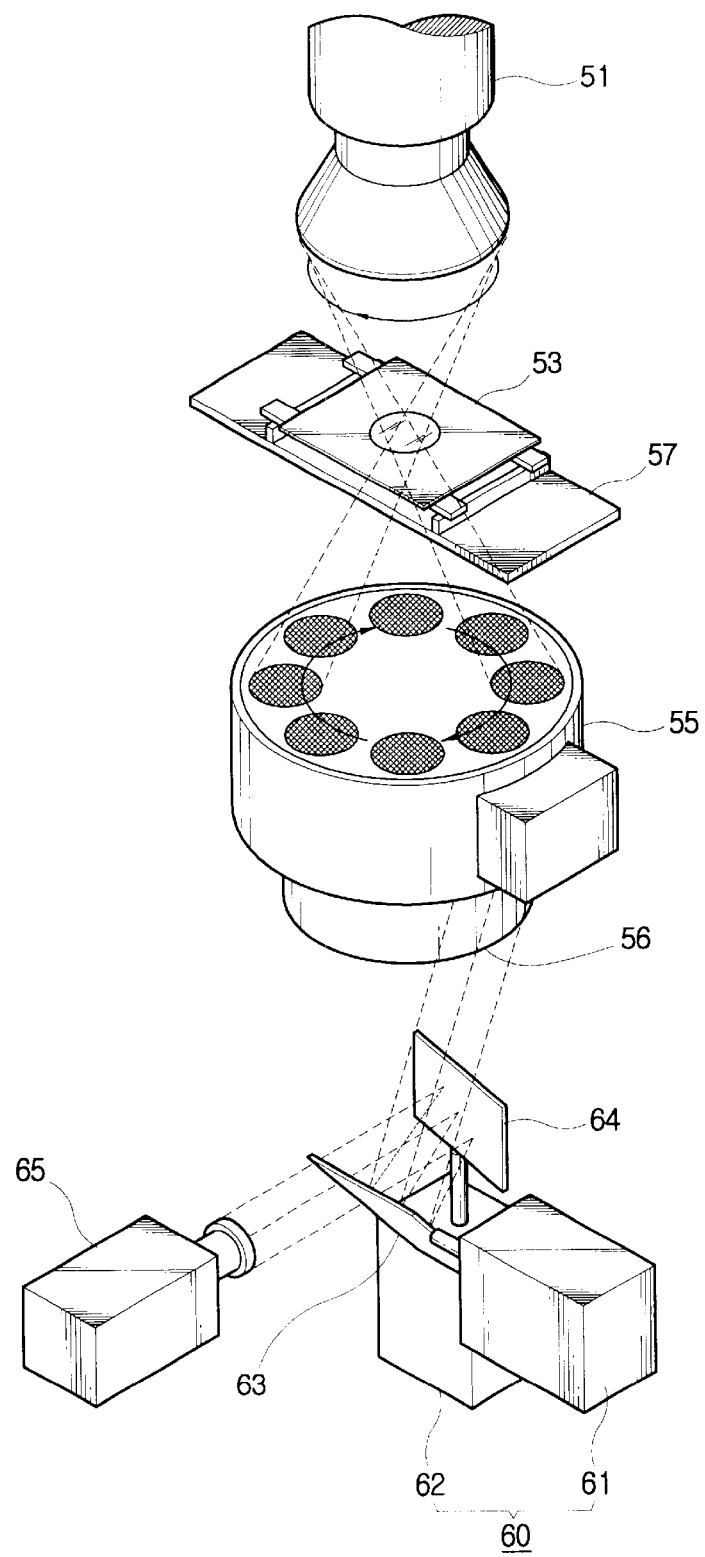
FIG. 4 schematically shows a perspective view of a conventional radiation inspection system.
Figure 5:
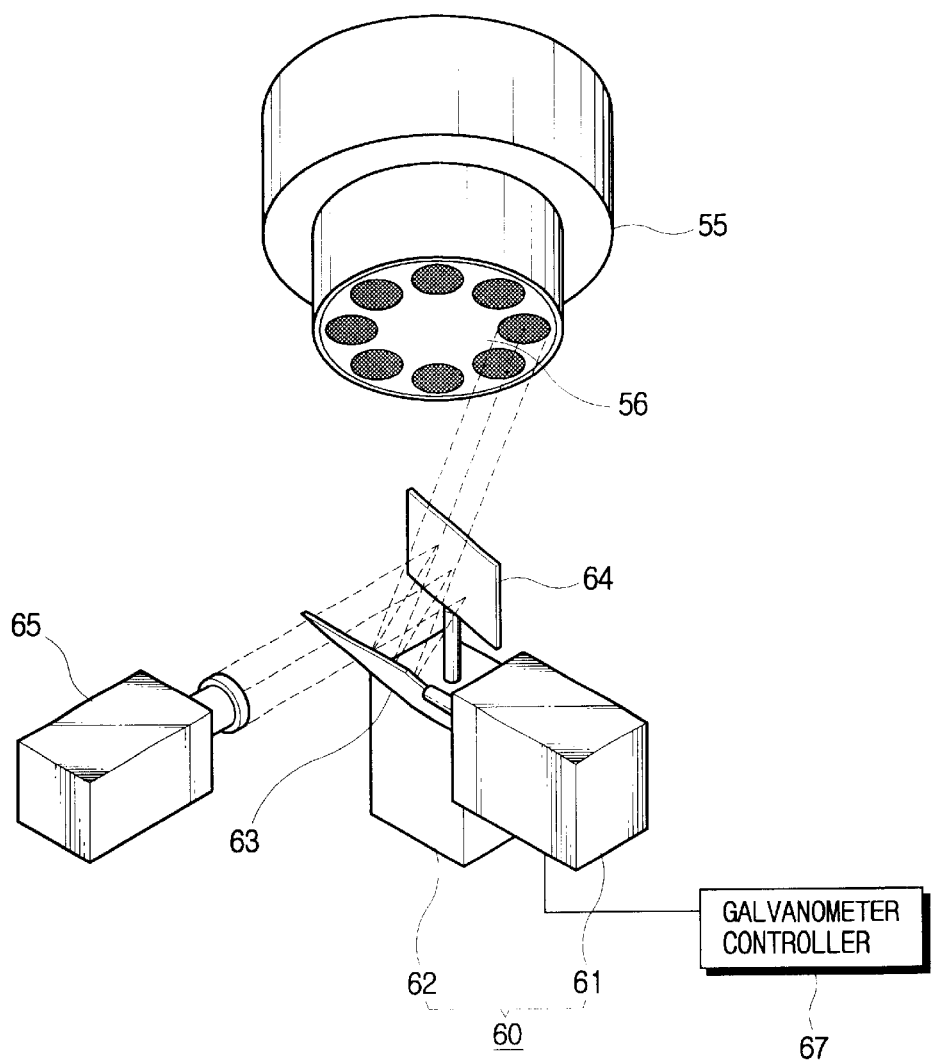
FIG. 5 shows a perspective view of some elements of FIG. 4 from a different angle.

Next, the visual images are photographed by the CCD camera 15 after passing through the polarizing filters 13 of the electronic shutter 10 as illustrated in FIG. 3. According to the present embodiment, the steering X-ray electronic tube 1 radiates the X-rays eight times onto the object 3 along the rotary direction thereof, and eight visual images are formed in sequence on the visual image part 6 by the X-rays which passed through the object 3. The respective polarizing filters 13 are supplied with electric power synchronously with formation of the corresponding visual images. Therefore, the electric power is supplied to the respective polarizing filters 13 in sequence when the respective visual images are formed. The respective visual images pass through the polarizing filters 13 sequentially eight times. The visual images having passed through the polarizing filters 13 are photographed by the CCD camera eight times.

As described above, according to the present invention, the visual images projected on the visual image part 6 are directly photographed by the CCD camera 15 by using the plurality of polarizing filters 13 formed of an LCD or a PDP capable of transmitting light when electric power is supplied. Accordingly, distortion of visual images or delay in time often caused by the conventional galvanometers can be prevented. Additionally, a cost of production can be reduced in comparison with the conventional system using the plurality of image intensifiers and the plurality of CCD cameras corresponding thereto.

As described above, according to the present invention, a prompt and exact inspection result can be achieved and a cost of production can be saved by using an electronic shutter transmitting visual images sequentially.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A radiation inspection system comprising:
   a steering radiation electronic tube for projecting radiation onto an object to be inspected;
   an image intensifier for converting a plurality of projection images formed by the radiation from the steering radiation electronic tube into visual images, said image intensifier having a visual image part on which the visual images are projected;
   an electronic shutter having a visual image transmission part for transmitting the visual images projected on the visual image part of the image intensifier in sequence; and
   a camera for photographing the visual images from the visual image transmission part of the electronic shutter in sequence.

2. The system according to claim 1, wherein electric signals are applied synchronously with formation of the visual images to the visual image transmission part causing the sequential transmission of the visual images thereby.

3. The system according to claim 2, wherein the visual image transmission part comprises a plurality of polarizing filters for transmitting or shielding the visual images according to the electric signals received thereby.

4. The system according to claim 3, wherein the polarizing filters are formed of one of a liquid crystal display or a plasma display panel.

5. The system according to claim 3, wherein the visual images are formed sequentially along a circumferential direction of the visual image part, and the polarizing filters are disposed along a circumferential direction of the visual image transmission part so as to be correspondent with the visual images.

6. The system according to claim 1, wherein the radiation includes X-rays.

7. A radiation inspection method using a radiation inspection system comprising the steps of:
   projecting radiation from a steering radiation electronic tube onto an object to be inspected;
   converting with an image intensifier a plurality of projection images formed by the radiation from the steering radiation electronic tube into visual images, said converting step including projecting the visual images onto a visual image part;
   providing an electronic shutter having a visual image transmission part corresponding to the visual images adjacent the visual image part;
   transmitting the visual images of the visual image part sequentially through the visual image transmission part; and
   photographing the visual images passing through the electronic shutter in sequence.

8. A method according to claim 7, wherein the transmitting step includes applying electric signals synchronously with formation of the visual images to the visual image transmission part.

9. A method according to claim 8, wherein the visual image transmission part comprises a plurality of polarizing filters for transmitting or shielding the visual images, and said transmitting step includes applying of the electric signals to the polarizing filters.

10. A method according to claim 9, wherein the polarizing filters are formed of a liquid crystal display or a plasma display panel.

11. A method according to claim 9, wherein the converting step includes sequentially forming visual images along a circumferential direction of the visual image part, and wherein said providing of an electronic shutter step includes disposing of the polarizing filters along a circumferential direction of the visual image transmission part so as to be correspondent with the visual images.

12. The method according to claim 7, wherein the radiation projected from the steering radiation electronic tube includes X-rays.

* * * * *